United States Patent
Kritzinger et al.

[11] Patent Number: 5,984,913
[45] Date of Patent: *Nov. 16, 1999

[54] CORNEAL ASPIRATION CANNULA AND METHOD OF USING

[75] Inventors: Michael S. Kritzinger, Johannesburg, South Africa; Stephen A. Updegraff, Rapid City, S. Dak.

[73] Assignee: Michiel S. Kritzinger, South Africa

[ * ] Notice: This patent issued on a continued prosecution application filed under 37 CFR 1.53(d), and is subject to the twenty year patent term provisions of 35 U.S.C. 154(a)(2).

[21] Appl. No.: 08/660,189

[22] Filed: Jun. 3, 1996

Related U.S. Application Data

[60] Provisional application No. 60/001,592, Jul. 27, 1995.

[51] Int. Cl.$^6$ .................................................. A61M 25/00
[52] U.S. Cl. .......................................... 604/541; 606/107
[58] Field of Search .................................. 604/19, 48, 73, 604/93, 128, 264, 289, 294, 297, 541; 606/107, 162; 433/96

[56] References Cited

U.S. PATENT DOCUMENTS

| | | | |
|---|---|---|---|
| 2,670,539 | 3/1954 | Wall | 433/96 |
| 2,696,047 | 12/1954 | Lanigan | 433/96 |
| 3,818,913 | 6/1974 | Wallach | 128/305 |
| 3,929,138 | 12/1975 | Curi | 128/304 |
| 4,357,941 | 11/1982 | Golubkov et al. | 128/316 |
| 4,406,285 | 9/1983 | Villasenor et al. | 128/305 |
| 4,417,579 | 11/1983 | Soloviev et al. | 128/303 R |
| 4,515,157 | 5/1985 | Federov et al. | 128/303 R |
| 4,705,035 | 11/1987 | Givens | 128/303 R |
| 4,739,761 | 4/1988 | Grandon | 128/305 |
| 4,744,360 | 5/1988 | Bath | 128/303.1 |
| 4,963,142 | 10/1990 | Loertscher | 606/14 |
| 5,171,213 | 12/1992 | Price, Jr. | 604/294 |
| 5,226,905 | 7/1993 | Hanna | 606/166 |
| 5,234,436 | 8/1993 | Eaton et al. | 606/107 |
| 5,250,062 | 10/1993 | Hanna | 606/166 |
| 5,312,330 | 5/1994 | Klopotek | 604/49 |
| 5,314,439 | 5/1994 | Sungita | 606/166 |
| 5,320,113 | 6/1994 | Tan | 128/858 |
| 5,342,378 | 8/1994 | Giraud et al. | 606/166 |
| 5,407,441 | 4/1995 | Greenbaum | 604/280 |
| 5,425,637 | 6/1995 | Whitehouse et al. | 433/96 |
| 5,569,280 | 10/1996 | Kamerling | 606/107 |
| 5,643,236 | 7/1997 | Linder | 604/264 |

FOREIGN PATENT DOCUMENTS

| | | | |
|---|---|---|---|
| 2539298 | 7/1984 | France | 604/264 |
| 0484679 | 3/1970 | Switzerland | 604/264 |
| 2247176 | 2/1992 | United Kingdom . | |

Primary Examiner—Mark Bockelman
Attorney, Agent, or Firm—Wood, Herron & Evans, L.L.P.

[57] ABSTRACT

An aspiration cannula is used in tectonic lamellar keratoplasty. The cannula is hand manipulatable and aspirates irrigation fluid and repositions a corneal cap or flap during corneal surgery. The cannula comprises a hand manipulatable elongated tube having an inlet end with a plurality of ports spaced apart along the length of the tube for aspirating irrigation fluid around a corneal incision interface and an outlet end for disposing the fluid.

15 Claims, 1 Drawing Sheet

CORNEAL ASPIRATION CANNULA AND METHOD OF USING

RELATED APPLICATIONS

This application is related to Provisional Application Ser. No. 60/001,592, filed Jul. 27, 1995, entitled "LASIK Marker, Irrigation Cannula, Corneal Flap/Cap Elevator, Method for Reducing Irregular Astigmatism and Debris/Epithelium in the Interface During a Lamellar Corneal Flap/Cap Surgery" which is incorporated herein in its entirety by reference. This application is also related to Applications Ser. Nos. 08/561,541, 08/562,257, 08/562,253 and 08/561,744, filed Nov. 22, 1995, entitled, "Corneal Surface Marker and Marking Method for Reducing Irregular Astigmatism During Lamellar (LASIK) Corneal Surgery", "Corneal Flap/Cap Elevator", "Method for Reducing Irregular Astigmatism and Debris/Epithelium in the Interface During Lamellar Corneal Flap/Cap Surgery", and "Corneal Irrigation Cannula and Method of Using", respectively, and Continuation-in-Part Application Ser. No. 08/624,027, filed Mar. 27, 1996, entitled "Corneal Surface Marker and Marking Method for Improving Laser Centration", which are all incorporated herein in their entireties by reference.

BACKGROUND OF THE INVENTION

Lamellar corneal surgery has undergone a steady evolution. Advancements in the technology, such as automated keratomes and non-freeze, no-suture techniques have markedly improved safety and effectiveness. When Dr. Luis Ruiz introduced the automated keratome and the in situ non-freeze, no-suture technique to the lamellar bed, other physicians embraced this and have since introduced this technique to thousands of surgeons worldwide. Although a significant advancement, even Dr. Luis Ruiz realized the relative imprecision of making a refractive pass with the keratome. He quickly learned to utilize the excimer laser to precisely reshape the cornea underneath the lamellar corneal flap. The precision achieved has been unparalleled, especially for the moderate to higher myopes.

Worldwide there have been many other surgeons that deserve credit for pursuing the combination of excimer laser with lamellar surgery. As surgeons began doing lamellar corneal surgery, they became concerned about the potential for inducing irregular astigmatism as well as introducing debris such as epithelial inclusions in the stromal interface. Fortunately, with the introduction of the automated keratome and non-freeze, non-suture techniques, irregular astigmatism rates are reduced but still pose a great problem. Debris in the interface also continues to be a chronic problem. Many surgeons have resorted to never wearing gloves during lamellar surgery just for that reason. Although infections in lamellar surgery are quite low, infection percentages, however low, need to be reduced and preferably eliminated. At present, it is unclear whether or not wearing gloves during lamellar surgery is the standard of care. Thus, we need a way to perform lamellar surgery with gloves safely so as not to introduce debris into the interface.

Recently a very famous clinical researcher in excimer laser technology expressed that his job is now to make surface ablation PRK (photorefractive keratectomy) as good or better than LASIK (laser assisted in situ keratomileusis). Preserving all the layers of the cornea provides quicker visual recovery and the predictability is less dependent on the ablation characteristics of the laser. Thus, LASIK in its infancy already has a head start over any surface ablation technique. Secondly, while PRK retreatment is not predictable, LASIK enhancement is possible. The tremendous amounts of research and development required to create the perfect surface ablation could be better spent in perfecting LASIK for all ranges of refractive errors.

There is a growing need to introduce lamellar surgery skills to surgeons new to this arena. Surgeons who have been performing ALK (automated lamellar keratoplasty) will be prepared to make an easy transition to LASIK. Many of the surgeons making the transition from PRK to LASIK appear totally consumed in what type of ablation to use in the bed, when in reality their primary concerns should be a safe keratectomy and repositioning the corneal cap/flap so that there is the least likely chance for debris in the interface causing irregular astigmatism. If that can be consistently reproduced, then enhancement is possible and predictability of the ablation for each surgeon will increase with experience.

SUMMARY OF THE INVENTION

This invention is directed to an improvement in instrumentation and surgical technique for reducing irregular astigmatism and debris/epithelium in the interface during lamellar corneal surgery. More particularly, an aspiration cannula for use in removing irrigation fluid surrounding a corneal interface and a method of using the cannula is provided by this invention.

In its most preferred form, the aspiration cannula for use in tectonic lamellar keratoplasty comprises a hand manipulatable, elongated and angled tube having an inlet end with four aspirating side ports radially spaced along the length of the tube for aspirating irrigation fluid from different directions. Each of the aspirating ports is approximately 19 gauge in diameter. Two of the side ports are located approximately 2.5 mm from an aspirating end port situated at the tip of the inlet end while the other two side ports are located approximately 5.0 mm from the end port of the inlet end. The cannula also has an outlet end for disposing of the fluid.

Most preferably, the aspirating side ports are radially space approximately 90 degrees from each other in a position whereby two aspirating side ports radially spaced approximately 180 degrees from each other are located approximately 2.5 mm along the length of the inlet end from two other aspirating side ports radially spaced approximately 180 degrees from each other. This configuration allows access to irrigating fluid from all sides of the aspiration cannula eliminating the need to rotate it during surgery. Further, having a plurality of aspirating ports also provides constant suction. Even if one or two aspirating ports are occluded with conjunctiva, aspiration may still take place.

A method of aspirating a corneal incision and repositioning a corneal cap or flap during lamellar surgery is also provided. The method preferably comprises inserting a corneal irrigating cannula into the interface of an overlying corneal cap or flap and corneal bed for the delivery of suitable fluid thereto, delivering the fluid under low flow through irrigating ports from the center of the corneal bed moving peripherally toward the edge of the bed and cap or flap, irrigating the interface with the fluid by gently elevating the overlying cap or flap and washing residual debris and epithelium from the corneal bed, and gently massaging the corneal cap of flap from the center of the corneal interface to the periphery removes residual fluid from the corneal surface by squeezing remaining irrigation fluid from the corneal interface to a gutter for aspiration and adheres the cap or flap to the stromal bed. Accurately aligning and repositioning the cap or flap to its correct anatomical position is achieved by using preoperative radial and pararadial marks while massaging the corneal cap or flap.

These and other advantages of the present invention will become more apparent from the drawing and detailed description.

DETAILED DESCRIPTION OF THE INVENTION

I. OVERVIEW OF THE SURGICAL PROCEDURE (LASIK)

Figure 1:
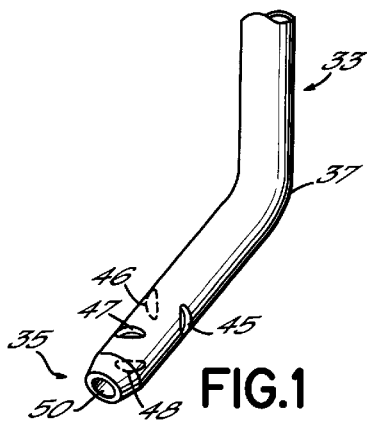
FIG. 1 illustrates a side view of an angled aspiration cannula of the present invention.

Prior to a lamellar dissection, a marker is used to outline the present anatomical surface of the cornea. Once the lamellar dissection is made and it is appropriate to return the corneal cap/flap to its proper anatomic position, the corneal bed is irrigated with low flow. The flap/cap is returned. Fluid is aspirated from the fornices such that fluid flows from the bed (top of the dome of the eye) out and downward to the fornices. This first step removes debris and epithelium from the interface. Irrigation should start centrally and move peripherally. The second step requires the suction cannula or aspirator to be placed gently on the edge of the keratectomy to prevent debris/epithelium from wicking back under the flap/cap. With a layer of irrigation fluid in the interface, the corneal flap/cap is then aligned with the preoperative surface marking. If debris continues to be present or the cap is not aligned, the method is repeated.

A. Preoperative ALK or LASIK
1. Eye Prep

We recommend mild lid scrubs to the eyelid margins. Patients diagnosed with meibomianitis or blepharitis should be adequately treated prior to surgery. This may include a short term use of systemic Tetracycline to help reduce meibomian secretions prior to surgery. Be sure to confirm that the patient is not pregnant and is not planning to become pregnant over the next six months as this may affect the outcome of the surgery.

2. Irrigation of the Fornices

A thorough irrigation of the inferior fornices and glove with cool BSS should be conducted. As many have noticed for a long time during cataract surgery when meibomian secretions present as a layer in a pool of irrigating solution, a quick irrigation with the l&A with the head tilted will remove this oily film in a large sheet. This is what we believe is happening when they tilt the patient's head and have already done the lid scrubs and irrigate the fornices. Thus, meibomian secretions are not present during the keratectomy.

3. Eye Drops a. Pilocarpinte 2% is used before the marking ring over the constricted pupil.

b. Light Reflex Constriction

This can be a little more difficult for patients to fixate. It prevents pharmacologic decentration of the pupil and probably is the most accurate way to achieve centration over the entrance pupil.

B. Operative
1. Draping

This is one of the most important steps. Whatever drape you plan to use, it must retract the eyelashes out of the field and the drape should not restrict the speculuni from opening fully so that adequate exposure of the globe can be obtained for suction. We presently use a 10–24 drape made by 3M to accomplish this.

2. Irrigation System

At present, we have been using the roller clamp on the IV bottle to control the flow of the BSS Plus through the irrigation cannula. We have found that it is best if this flow is just adequate to float a cap or flap off the bed without creating distortions, undulations or undue turbulence. This irrigation can also be used to irrigate the globe and cornea prior to surgery.

3. LASIK Marking System

Lamellar corneal surgery has undergone many changes in instrumentation and technique. The most recent advancement is excimer laser in situ keratomileusis or LASIK. This is a non-freeze, non-suture technique that incorporates the precise reshaping of the corneal stroma with the laser and the minimal wound healing/quick recovery of lamellar corneal surgery. A major complication of lamellar surgery, which can be sight threatening, is irregular astigmatism. To date, corneal surgeons have used subtle and often imperceptible visual cues to reapproximate the flap or corneal tissue. It is apparent that a slight decentration or disorientation of the flap can result in irregular astigmatism. We propose the concept of a corneal surface marker, the Kritzinger-Updegraff (KU) LASIK marker, to improve centration of the procedure and the precise repositioning of the corneal cap or flap. This marker was developed to permit a centered keratectomy which is dependent upon an outer ring on which the surgeon centers the suction ring. The marker also has six radial and two pararadial marks within it. These radial marks vary in width which permits precise repositioning of the cap or flap edges. This prevents micro-decentration seen when the surgeon uses an "equally gapped gutter" as the cue for alignment. The pararadial marks aide in preventing a reversed free cap.

The corneal surface marker consists of two concentric rings; one 5 mm in diameter with cross-hair (to aid centering) and 10 mm to 10.5 mm in diameter radiating off the center ring are six radial and two pararadial marks. The width of the superior and inferior radials as well as one temporal pararadial are two times thicker than the other radials. The pararadials at 11:00 and 1:00 are of different width to ensure proper orientation of a free cap and prevent placement of a free cap upside down (epithelial surface down). The concentric rings ensure centration of the mark and subsequent centration of the LASIK suction ring. The different widths of the pararadials and radials permit accurate, anatomic repositioning of the cap or flap with microsurgery. The radiating marks extend beyond the outer ring to provide adequate reference points with the large flaps made with the LASIK suction ring.

4. Centration a. Positioning the Patient's Head

The goal is to have the globe absolutely centered in the patient's socket as the patient fixates on the red fixation beam. An attempt should be made to position the patient's chin and forehead so that the globe is on a flat plane. It is important to make sure that the chin cannot move up or down and the head must be stable so that it cannot turn left or right. Once you have the globe centered within the orbit and looking straight ahead, use the joy stick of the X axis to bring the patient "dead" center in the cross-hairs that are in the optics of the right eye piece. The KU corneal marker is then positioned so that the superior and medial lateral marks of the cross-hair match with those of the marker. Thus, after creating the mark the cross-hairs can be superimposed upon it. If there is not absolute correspondence of the cross-hairs in the mark that is placed on the cornea, the surgeon is then responsible to make a "mental note" of this orientation when ablating the stromal bed and putting the flap back into position. At this point with the Keracor 116 laser, the red and green light must be superimposed prior to placing these marks or the cross-hair will move away from the center of the pupil after these maneuvers have been performed.

b. Applying the Suction Ring

It is important to have the circular mark of the KU marker aligned concentrically with the suction ring. This ensures that the flap will be central to the pupil.

c. Ablation

After the keratectomy is performed, the flap is folded back nasally. The peripheral markings of the KU marker are still visible. Thus, these are used as a visual cue to line up the cross-hair of the redicule which correspond to the exact fixation prior to the keratectomy. It is very important not to move the joy stick of the excimer laser at this point to center the ablation. Rather, move the patient's head gently to achieve centration. Improper alignment of the patient's head does not mean the bed has moved but rather the patient'shead has moved and thus must be oriented back to the position you had initially worked so hard to achieve. Do not play with the joy stick.

d. Added Security Measures

When using the Keracor 116 laser, leave all three lights on; two red lights and one green light. The one red light with a green indicates that as you are lasering you are at the correct level of focus. The other red light follows the actual laser and indicates the orientation of the laser beam whether it is astigmatism or spherical correction. This is an added security measure to ensure that you are lasering the proper axis.

e. Centering Pearl

When you are lasering, turn the light down and ask the patient continuously to look into the red fixation light. This is a cross-check to ensure that the patient is centering on the cross-hair and that the laser treatment is in the center of the pupil. Between each zone of treatment, we recommend either using a spatula or hockey stick to wipe excess fluid from the stromal surface.

f. Addendum to Centration

Eye trackers can be very helpful, however, we feel that these steps in centering the globe are much more fail-safe and ultimately efficient.

5. Suction Rings a. Adjustable Ring

The adjustable suction ring can be used for LASIK, however, this consistently creates a small flap or cap. On average, the diameter is 7.2 mm. For standard ALK cases, we do not recommend routinely trying to use the excimer laser suction ring because the grooves in the sclera that this creates do not match the adjustable suction ring and it can be difficult to center your suction ring for the very critical refractive pass with standard ALK.

b. LASIK Suction Ring

This ring has a larger inside diameter than the adjustable suction ring and it allows the keratome to be exposed to more cornea thus creating keratectomies which are on the average 8.55 mm in diameter. This is the suction ring of choice for LASIK. However, when placing this suction ring on a globe that retropulses fairly freely, it is important to proptose the globe with a speculum so that the suction ring has a firm adherence to the globe prior to initiating suction. Because the outside of the LASIK suction ring is a smaller diameter than the adjustable suction ring, firm pressure on the suction ring handle can retropulse the globe and thus make it difficult to have clearance for the keratome. The adjustable suction ring on the other hand has a large place that will rest on the eyelids and if the globe is proptosed it will be held by the suction of the suction ring and in turn the suction plate will be held upwards by the lids thus providing easier exposure. This will become of less significance as surgeons gain experience with the fixed LASIK suction ring.

6. Laser Ablation

Remember to center with KU marker cues before performing laser ablation of the corneal stroma.

7. Irrigation Cannula and Technique For Low Flow Techtonic Lamellar Keratoplasty The details of the irrigation cannula and technique are disclosed in pending Application Ser. No. 08/561,744, filed, Sep. 19, 1995, which is incorporated herein by reference in its entirety.

With the most recent advancement of eximer laser in situ keratomileusis and its popularization, it has become necessary to develop instruments which will reduce the most significant complications of lamellar surgery: irregular astigmatism and debris/epithelium in the interface. we described above a method and instrument for marking, aligning and returning the overlying corneal flap to its correct anatomical position. We now describe in detail an irrigating cannula and technique that will remove debris from the interface and improve on the problem of postoperative irregular astigmatism stemming from lamellar keratoplasty.

Once the keratectomy is made, an anterior chamber irrigating cannula is introduced underneath the cap or flap and into the interface between the corneal flap or cap and stromal bed. Preferably, the cannula has an angled stem or handle which enables the introduction into the interface. As previously mentioned briefly, the irrigation flow should be adjusted so that the cap/flap floats gently above the stromal bed. The goal is to have the patient fixating so that the apex of the globe is in line with the microscope. This allows the fluid to flow from underneath the cap or flap peripherally and out past the limbus into the fornices of the eye. After approximately 15 to 20 seconds of this form of irrigation, the irrigating cannula can be moved centrally towards a stromal hinge (if any exists) and gently swept back and forth from the hinge and then held centrally again. This allows any epithelium entrapped by the blade at the hinge to be freed and irrigated out.

In one form, the irrigating cannula for use between corneal flap or cap and the stromal bed has three 25 gauge irrigating ports on its end. One of these ports, located at the tip of the cannula will deliver low flow irrigating fluid directly from the tip. The other two ports will be approximately 90 degrees away with one elevated and angled superiorly and one angled inferiorly. On low flow with balanced salt solution, the irrigating cannula with its unique port configuration generates a flow pattern indicated by arrows that very gently elevates and suspends the overlying corneal flap or cap while washing debris and epithelium to the inferior fornix. The constant irrigation of the bed, which is at the apex of the dome of the cornea and globe, will allow debris to be removed from the interface preventing postoperative irregular astigmatism.

By utilizing the preoperative markings from the above described Kritzinger/Updegraff LASIK marker and marking method, the cornea is gently massaged so the cornea is returned into the correct anatomical position. If any wrinkling of the corneal cap or flap is evident or there is not correct alignment of any of the eight (8) radial or pararadial marks, then the irrigating cannula is reintroduced and the cap or flap repositioning procedure is performed again.

We are presently using curved tying forceps or other suitable instrumentation to smooth the flap or cap back over the corneal stroma making sure the preoperative radial and pararadial marks are aligned. If alignment of the marks is not achieved, the irrigating cannula is once again reintroduced while the cap is allowed to be adjusted on a bed of fluid.

II. ASPIRATION CANNULA AND METHOD

The present invention and its advantages will be better understood from the above outlined stages of the surgical procedure and the following detailed description incorporating references to the accompanying drawing figures. In the various figures, like reference characters are used to designate like parts.

A. Aspiration Cannula and Technique

With the most recent advancement of excimer laser in situ keratomileusis and its popularization, it has become necessary to develop instruments which will reduce the most significant complications of lamellar surgery: irregular astigmatism and debris/epithelium in the interface. We described above a method and instrument for making, aligning and returning the overlying corneal flap to its correct anatomical position and an irrigating cannula and technique that will remove debris from the interface and improve on the problem of post operative irregular astigmatism stemming from lamellar keratoplasty. We now describe in detail an aspiration cannula and technique that will aspirate and remove debris from a corneal keratectomy and fornices of the eye while returning and smoothing the overlying corneal cap or flap to its correct anatomical position.

Referring to FIG. 1, aspiration cannula 33 is preferably an angled, elongated 19 gauge tube. Further, the tube is hand manipulatable. Cannula 33 has an inlet end 35 located approximately 10 mm from the angle shown generally at 37. Preferably, inlet end 35 has four aspirating side ports, 45, 46, 47, and 48, and one end port 50 located at the tip of the tube. Each port is approximately 19 gauge in diameter and is adequate to aspirate epithelium, debris and lint during irrigation of the corneal interface. The side ports are located approximately 2 mm from end port 50 spaced along the length of cannula 33. They are also radially spaced approximately 90 degrees from each other. This allows access to irrigating fluid from all sides of cannula 33 eliminating the need to rotate it during surgery. Further, having a plurality of aspirating ports also provides constant suction.

Even if one or two aspirating ports are occluded with conjunctiva, aspiration may still take place.

Figure 2:
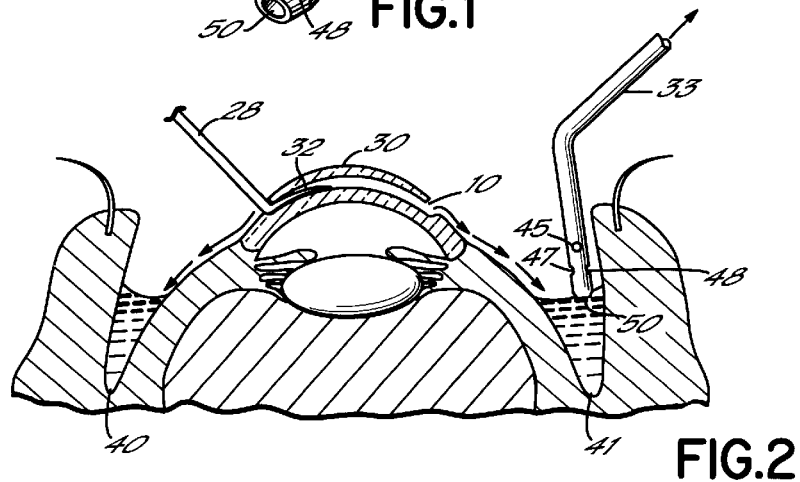
FIG. 2 illustrates a side view of an angled aspiration cannula of the present invention eliminating epithelium and debris from the fornices of the eye.

With reference to FIG. 2, once the keratectomy is made, an anterior chamber irrigating cannula 28 is introduced underneath the flap and into the interface between corneal flap or cap 30 and stromal bed 32. As previously mentioned, the irrigation flow should be adjusted so that the cap/flap floats gently above the bed. The goal is to have the patient fixating so that the apex of the globe is in line with the microscope. this allows the fluid to flow from underneath the cap or flap peripherally and out past the limbus into the fornices 40 and 41.

Figure 4:
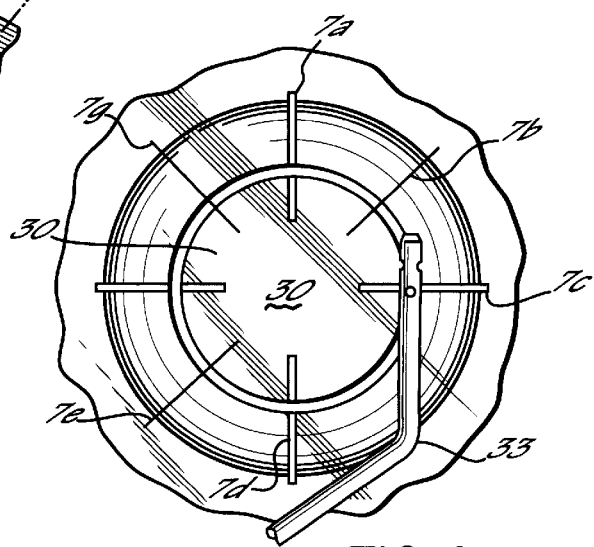
FIG. 4 illustrates a perspective top view of an angled aspiration cannula of the present invention wherein the desired aspiration pattern through the ports of the cannula gently removes debris and particulate from the periphery of the corneal flap or cap and stromal bed interface. Also illustrated are the preoperative markings that aid in alignment of the cap or flap when using the aspirating technique.

Subsequent to irrigation, the fornices 40 and 41 can be aspirated with the gently suction of aspiration cannula 33. This removes epithelial debris and lint from the surrounding area that may wick back into the corneal interface. After approximately 15 to 20 seconds of irrigation, the irrigating cannula 28 can be moved centrally toward the stromal hinge (if there is a flap instead of a cap) and gently swept back and forth from the hinge and then held centrally again constantly irrigating the corneal interface. This allows any epithelium entrapped at the hinge to be freed and irrigated out. As shown in FIG. 4, once the fornices 40 and 41 are cleared of fluid, aspiration cannula 33 can be moved toward the gutter 10 concurrent with low flow irrigation or pst irrigation with only the residual underlying irrigation fluid remaining. The cap or flap 30 can then be massaged and nudged with cannula 33 so that radial and pararadial preoperative marks are fairly aligned. Marks radiating from central zone 31 of corneal cap or flap 30, shown in the figure as 7a, 7b, 7c, 7d, 7e, 7f, 7g and one pararadial shown as 7z, extend a length sufficient to cross and provide adequate reference points past gutter 10. These radial and pararadial marks vary in width which permits precise repositioning of the cap or flap edges after the keratectomy and laser ablation have been performed. Once the marks are aligned, the gutter 10 should be aspirated 270 degrees while there is steady irrigation. This again removes debris that could have hung up at the edge of the keratectomy and not run to the fornices 40 and 41. Aspiration of the gutter 10 is continued as the irrigating cannula is gently withdrawn from the interface taking note of the approximation of the radial and pararadial marks.

Figure 3:
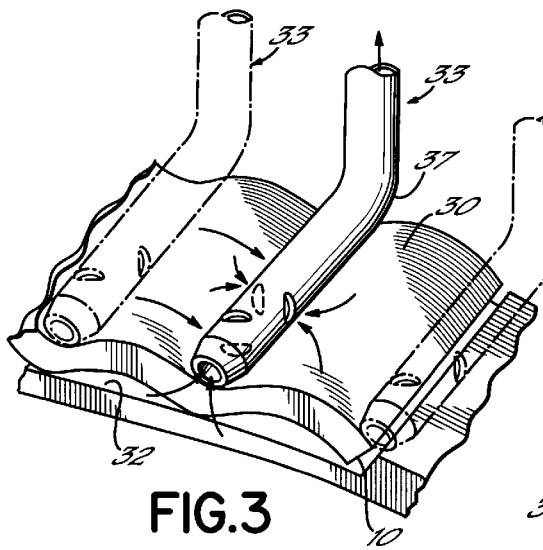
FIG. 3 diagrammatically illustrates an enlarged perspective side view of an angled aspiration cannula and technique of the present invention wherein an aspiration cannula engages a corneal flap surface and gently massages and repositions the corneal flap into the stromal bed while aspirating residual fluid and debris that remains around the corneal interface through a plurality of ports. The aspiration flow pattern through the tip and side ports of the cannula is also demonstrated.

As shown in FIG. 3, gentle massage of the corneal cap or flap with aspiration cannula 33 removes the remaining irrigation fluid surrounding the corneal interface while accurately aligning and repositioning cap or flap 30 to its correct anatomical position. We are presently using a curved tying forceps or other suitable instrumentation to smooth the flap or cap 30 back over the corneal stroma 32 prior to massaging with aspiration cannula 33. Thereafter, the aspiration cannula is moved across the top of the cap or flap 30 in a gentle massaging motion from the center to the periphery making sure the radial and pararadial marks are aligned thereby removing residual fluid from the corneal surface and squeezing remaining fluid from the interface to gutter 10 to be aspirated out. If alignment is not achieved, the irrigating cannula is once again reintroduced and aspiration is performed in the gutter 10 while the cap 30 is allowed to be adjusted on a bed of fluid.

Referring again to FIG. 4, the final maneuver is to aspirate with suction cannula 33 residual fluid from the gutter 10 out of the keratectomy to ensure that no particles will be wicked back into the interface once the fluid has decreased. This is done during and after low flow delivery of fluid from the center of the interrace to the periphery (towards the keratectomy) to adequately effect adherence of the corneal cap or flap 30 to the stromal bed 32.

By utilizing the preoperative markings from the above described Kritzinger/Updegraff LASIK marker and marking method, the cornea is gently massaged with aspiration cannula 33 so the cornea is returned into the correct anatomical position. If any wrinkling of the corneal cap or flap is evident or there is not correct alignment of any of the radial or pararadial marks, then the irrigating cannula is reintroduced and the cap or flap repositioning procedure is performed again.

B. Cap/Flap Adherence

1. Use of Air on Corneal Surface

Air blown on the surface of the cornea can be used working from the center of the corneal surface to the periphery for adherence to the cap/flap. This wicks out fluid from the center to the gutter which again improves the removal of debris and epithelial inclusions from the interface. We believe that there is a higher incidence of folds or cracks in Bowman's membrane when air is used. We also believe that using surface air requires one to work very quickly, because the cap will adhere very rapidly, thus it must be wellcentered before the air is introduced. Therefore, we prefer to use the aspiration cannula to very carefully aspirate the fluid from the gutter and out from underneath the cap/flap and to massage the fluid underneath the cap or flap from the center of the stromal bed to the periphery gutter for aspiration. Extreme care must be taken when using the cannula to remove the fluid in that the patient must have solid fixation. If the patient fixes incorrectly, the edge of the cap or flap will become bunched up and potentially dislodge the perfect orientation we had previously achieved with the irrigation and aspiration maneuver. However, we do find that with approximately three minutes of time the cap or flap is quite adherent by using this maneuver. Thus, the aspiration cannula makes drying the gutter and cap or flap interface fast, safe and efficient while obtaining proper and suitable adherence.

2. Adherence Tests a. Slade Stria Test

By taking a pair of curved tying forceps and gently depressing approximately 1–2 mm away from the keratectomy gutter, one can see folds or stria originating from the point of depression in the cornea up past the gutter and on the surface of the cap or flap. This should be seen for 360 degrees upon depression. If there are no stria two things are occurring, 1) the cap of flap has not adhered to the bed, and, 2) the cap of flap has possibly folded on itself on the edge and is preventing adherence of the cap or flap. With the merocel drying technique, we typically place a drop of BSS on the central cornea while drying the gutter. This improves postoperative visual recovery and aids in patient fixation.

b. Blink Test

Have the patient repeatedly blink his or her eyes following the Slade Stria Test to confirm the adherence of the cap or flap. One must be very cautious when removing the 10–24 drape. We typically remove the drape as we remove the lid speculum and that way the lid speculum retracts the drape away from the globe as we move them simultaneously. Caps and flaps have been dislodged upon removing speculums and are more likely when the edge of a sharp drape catches the keratectomy of the cap and either totally dislodges it or disorients it so that irregular astigmatism is present after surgery. On should always check with the blink test after the drape is removed.

It should be understood that the embodiments of the present invention shown and described in the specification are only preferred embodiments of the inventors who are skilled in the art and are not limiting in any way. Therefore, various changes, modifications or alterations to these embodiments may be made or resorted to without departing from the spirit of the invention and the scope of the following claims.

What is claimed is:

1. A cannula for aspirating irrigation fluid and repositioning a corneal cap or flap during corneal surgery comprising:

a suction source for aspirating irrigation fluid, a hand manipulatable elongated suction tube having an outlet end connected to said suction source and an inlet end for aspirating irrigation fluid, said tube is angled between the ends and has a plurality of ports spaced apart along the length of said tube between the inlet end and the tube angle for aspirating irrigation fluid by said suction source, said ports sized for aspiration of epithelium, debris and irrigation fluid during corneal surgery, said tube length having said ports for accurately aligning and repositioning the cap or flap to its correct anatomical position.

2. The aspiration cannula of claim 1 wherein each of said aspirating ports is approximately 19 gauge in diameter.

3. The aspiration cannula of claim 1 wherein said tube is angled approximately 10 mm from an inlet end.

4. The aspiration cannula of claim 1 wherein one of said aspirating ports is situated at a tip of said inlet end for the removal of irrigation fluid directly into said inlet end.

5. The aspiration cannula of claim 1 having at least two aspirating side ports spaced along the tube length from said inlet end for removing irrigation fluid around a corneal incision interface.

6. The aspiration cannula of claim 5 wherein said aspirating side ports are radially spaced approximately 90 degrees from each other.

7. The aspiration cannula of claim 5 wherein said aspirating side ports are radially spaced approximately 90 degrees from an aspirating port at the tip of said end.

8. The aspiration cannula of claim 1 having four aspirating side ports radially spaced along the length of said inlet end, each of said side ports for removing fluid from different directions.

9. The aspiration cannula of claim 8 wherein two side ports are located approximately 2.5 mm from an aspirating end port situated at the tip of said inlet end and two side ports are located approximately 5.0 mm from said end port of said inlet end.

10. The aspiration cannula of claim 8 wherein said aspirating side ports are radially spaced approximately 90 degrees from each other.

11. The aspiration cannula of claim 8 having two aspirating side ports radially spaced approximately 180 degrees from each other located approximately 2.5 mm along the length of said inlet end from two other aspirating side ports radially spaced approximately 180 degrees from each other.

12. A cannula for aspirating irrigation fluid and repositioning a corneal cap or flap during corneal surgery comprising:

a suction source for aspirating irrigation fluid, a hand manipulatable, elongated and angled tube having an outlet end connected to said suction source and an inlet end for aspirating irrigation fluid, said tube is angled between the ends and has four aspirating side ports radially spaced along the length of said tube between the inlet end and the tube angle for aspirating irrigation fluid from different directions by said suction source, two of said side ports being located approximately 2.5 mm from an aspirating end port situated at the tip of said inlet end and the other two side ports being located approximately 5.0 mm from said end port of said inlet end.

13. The aspiration cannula of claim 12 wherein said aspirating side ports are radially spaced approximately 90 degrees from each other.

14. The aspiration cannula of claim 12 having two aspirating side ports radially spaced approximately 180 degrees from each other located approximately 2.5 mm along the length of said inlet end from two other aspirating side ports radially spaced approximately 180 degrees from each other.

15. The aspiration cannula of claim 12 wherein each of said aspirating ports is approximately 19 gauge in diameter.

* * * * *